(12) United States Patent
Kemp et al.

(10) Patent No.: US 9,205,199 B2
(45) Date of Patent: Dec. 8, 2015

(54) AUTO-INJECTOR WITH NEEDLE SHROUD AND NEEDLE PROTECTION CAP

(75) Inventors: Thomas Mark Kemp, Ashwell (GB); Timothy Donald Barrow-Williams, St. Albans (GB); Matthew Ekman, Macclesfield (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 409 days.

(21) Appl. No.: 13/580,271

(22) PCT Filed: Feb. 16, 2011

(86) PCT No.: PCT/EP2011/052304
§ 371 (c)(1), (2), (4) Date: Feb. 8, 2013

(87) PCT Pub. No.: WO2011/101382
PCT Pub. Date: Aug. 25, 2011

(65) Prior Publication Data
US 2013/0131602 A1    May 23, 2013

(30) Foreign Application Priority Data
Feb. 22, 2010   (EP) .................................... 10154191

(51) Int. Cl.
| | |
|---|---|
| *A61M 5/32* | (2006.01) |
| *A61M 5/20* | (2006.01) |
| *A61M 5/315* | (2006.01) |
| *A61M 5/46* | (2006.01) |
| *A61M 5/48* | (2006.01) |
| *A61M 5/24* | (2006.01) |
| *A61M 5/31* | (2006.01) |
| *F16H 25/20* | (2006.01) |

(52) U.S. Cl.
CPC ........... *A61M 5/3202* (2013.01); *A61M 5/2033* (2013.01); *A61M 5/326* (2013.01);
(Continued)

(58) Field of Classification Search
CPC . A61M 5/3202; A61M 5/2033; A61M 5/326; A61M 5/315; A61M 5/46; A61M 5/482; A61M 5/484; A61M 2005/0206; A61M 2005/208; A61M 2005/2086; A61M 2005/2418; A61M 2005/3103; A61M 2005/3152; A61M 2005/3247; A61M 2205/581; A61M 2205/583; F16H 25/2056; F16H 25/26
USPC ......... 604/131, 134–138, 187, 192, 194–197, 604/207–208, 212, 214, 222, 228, 232
See application file for complete search history.

(56) References Cited

U.S. PATENT DOCUMENTS
5,137,516 A * 8/1992 Rand et al. .................... 604/136
(Continued)

FOREIGN PATENT DOCUMENTS
FR           2583291       12/1986
(Continued)

OTHER PUBLICATIONS
International Search Report for Int. App. No. PCT/EP2011/052304, completed Mar. 9, 2011.
(Continued)

*Primary Examiner* — Theodore Stigell
*Assistant Examiner* — Amber Stiles
(74) *Attorney, Agent, or Firm* — Fish & Richardson P.C.

(57) ABSTRACT

An auto-injector may be used to administer a dose of a liquid medicament (M). In some embodiments, a shroud is arranged inside a housing, the shroud slidable in longitudinal direction between at least a retracted position, in which a hollow injection needle is exposable and an advanced position, in which the needle is covered by the shroud. A protective needle shield is attachable to the needle in a manner to partially protrude beyond the proximal end of the shroud through the orifice with the needle in its advanced position. A syringe carrier is arranged inside the shroud and comprises at least one snap for locking it to the shroud in order to prevent relative axial motion. The snap is configured to automatically disengage upon removal of the protective needle shield to allow the syringe and needle to be retracted into the covered position under load of the syringe spring.

14 Claims, 9 Drawing Sheets

(52) U.S. Cl.
CPC ............ *F16H25/2056* (2013.01); *A61M 5/315* (2013.01); *A61M 5/46* (2013.01); *A61M 5/482* (2013.01); *A61M 5/484* (2013.01); *A61M 2005/206* (2013.01); *A61M 2005/208* (2013.01); *A61M 2005/2086* (2013.01); *A61M 2005/2418* (2013.01); *A61M 2005/3103* (2013.01); *A61M 2005/3152* (2013.01); *A61M 2005/3247* (2013.01); *A61M 2205/581* (2013.01); *A61M 2205/583* (2013.01); *F16H 25/20* (2013.01)

(56) References Cited

U.S. PATENT DOCUMENTS

| | | | |
|---|---|---|---|
| 7,357,790 B2 * | 4/2008 | Hommann et al. | 604/198 |
| 2002/0095120 A1 | 7/2002 | Larsen et al. | |
| 2004/0000818 A1 | 1/2004 | Preuthun et al. | |
| 2013/0131595 A1 | 5/2013 | Ekman et al. | |

FOREIGN PATENT DOCUMENTS

| | | |
|---|---|---|
| FR | 2781857 | 2/2000 |
| WO | 01/89613 | 11/2001 |
| WO | 03/062672 | 7/2003 |
| WO | 2004/107975 | 12/2004 |
| WO | 2009/141650 | 11/2009 |

OTHER PUBLICATIONS

International Preliminary Report on Patentability for Int. App. No. PCT/EP2011/052304, mailed Sep. 7, 2012.

International Search Report issued in PCT/EP2011/052303 on Nov. 24, 2011 (2 pages).

International Preliminary Report on Patentability issued in PCT/EP2011/052303 on Sep. 7, 2012 (5 pages).

Restriction Requirement issued in U.S. Appl. No. 13/580,268 on Jun. 19, 2015 (6 pages).

\* cited by examiner

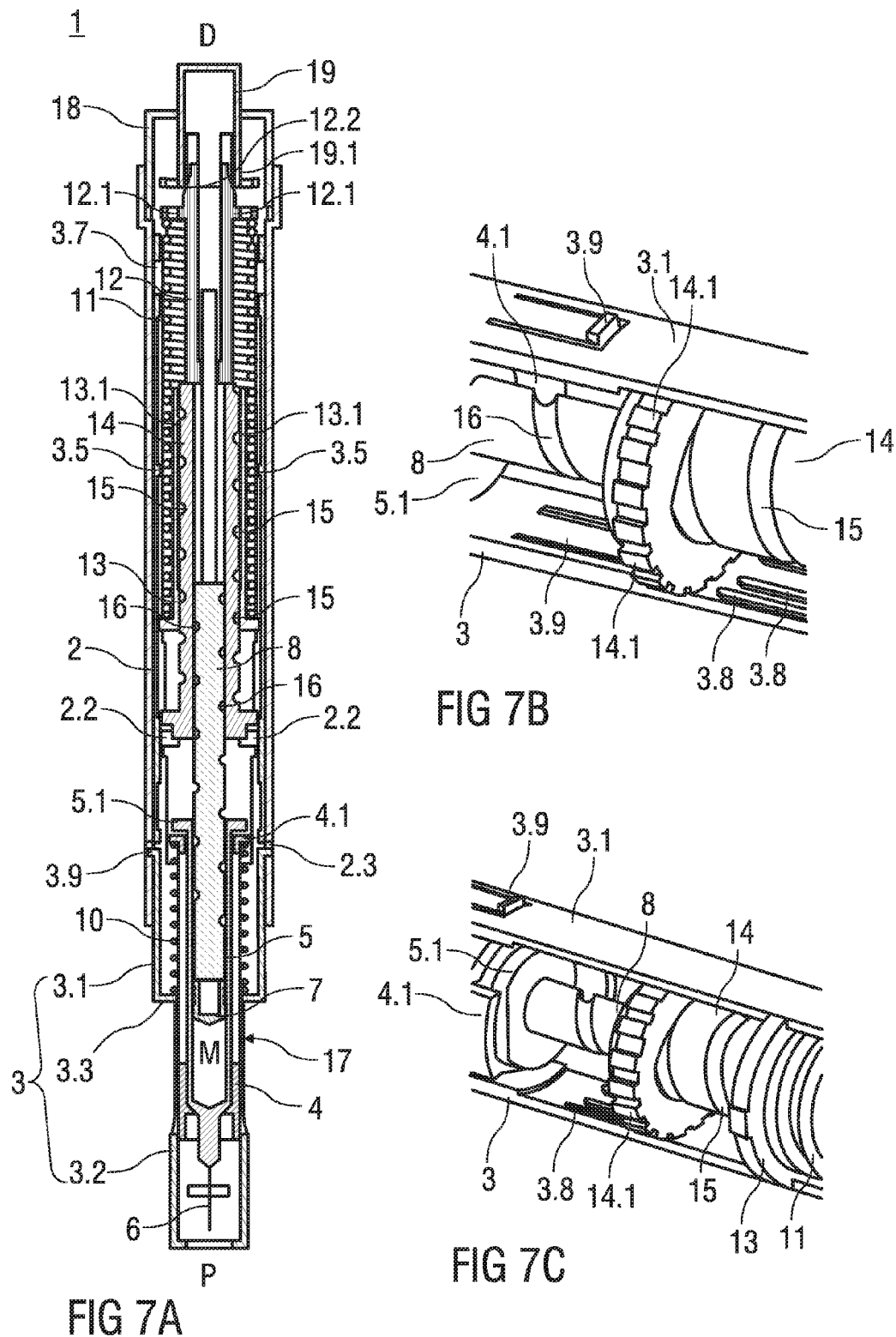

AUTO-INJECTOR WITH NEEDLE SHROUD AND NEEDLE PROTECTION CAP

CROSS REFERENCE TO RELATED APPLICATIONS

The present application is a U.S. National Phase Application pursuant to 35 U.S.C. §371 of International Application No. PCT/EP2011/052304 filed Feb. 16, 2011, which claims priority to European Patent Application No. 10154191.0 filed on Feb. 22, 2010. The entire disclosure contents of these applications are herewith incorporated by reference into the present application.

FIELD OF INVENTION

The invention relates to an auto-injector for administering a dose of a liquid medicament.

BACKGROUND

Administering an injection is a process which presents a number of risks and challenges for users and healthcare professionals, both mental and physical.

Injection devices (i.e. devices capable of delivering medicaments from a medication container) typically fall into two categories—manual devices and auto-injectors.

In a manual device—the user must provide the mechanical energy to drive the fluid through the needle. This is typically done by some form of button/plunger that has to be continuously pressed by the user during the injection. There are numerous disadvantages for the user from this approach. If the user stops pressing the button/plunger then the injection will also stop. This means that the user can deliver an underdose if the device is not used properly (i.e. the plunger is not fully pressed to its end position). Injection forces may be too high for the user, in particular if the patient is elderly or has dexterity problems.

The extension of the button/plunger may be too great. Thus it can be inconvenient for the user to reach a fully extended button. The combination of injection force and button extension can cause trembling/shaking of the hand which in turn increases discomfort as the inserted needle moves.

Auto-injector devices aim to make self-administration of injected therapies easier for patients. Current therapies delivered by means of self-administered injections include drugs for diabetes (both insulin and newer GLP-1 class drugs), migraine, hormone therapies, anticoagulants etc.

Auto-injectors are devices which completely or partially replace activities involved in parenteral drug delivery from standard syringes. These activities may include removal of a protective syringe cap, insertion of a needle into a patient's skin, injection of the medicament, removal of the needle, shielding of the needle and preventing reuse of the device. This overcomes many of the disadvantages of manual devices. Forces required of the user/button extension, hand-shaking and the likelihood of delivering an incomplete dose are reduced. Triggering may be performed by numerous means, for example a trigger button or the action of the needle reaching its injection depth. In some devices the energy to deliver the fluid is provided by a spring.

Auto-injectors may be disposable or single use devices which may only be used to deliver one dose of medicament and which have to be disposed of after use. Other types of auto-injectors may be reusable. Usually they are arranged to allow a user to load and unload a standard syringe. The reusable auto-injector may be used to perform multiple parenteral drug deliveries, where the syringe is disposed after having been spent and unloaded from the auto-injector. The syringe may be packaged with additional parts to provide additional functionality.

US 2002/0095120 A1 discloses an automatic injection device which automatically injects a pre-measured quantity of fluid medicine when a tension spring is released. The tension spring moves an ampoule and the injection needle from a storage position to a deployed position when it is released. The content of the ampoule is thereafter expelled by the tension spring forcing a piston forward inside the ampoule. After the fluid medicine has been injected, energy stored in the tension spring is released and the injection needle is automatically retracted back to its original storage position.

Usually the hollow needle is equipped with a protective needle shield for keeping the needle sterile and preventing it from being mechanically damaged.

In order to prepare the auto-injector for delivering a dose the protective needle shield has to be removed from the needle. This may be done by gripping the protective needle shield and pulling it away from the needle. This will usually result in an exposed needle which is undesirable in terms of needle safety. In order to solve that problem the needle and syringe could be arranged inside a needle shroud in a manner to hide the needle when the protective needle shield is removed. However, this would require the protective needle shield to be arranged inside the needle shroud, too, making it virtually inaccessible for a user to be gripped.

SUMMARY

It is therefore an object of the present invention to provide an auto-injector with an improved needle protection.

The object is achieved by an auto-injector according to claim 1.

Preferred embodiments of the invention are given in the dependent claims.

According to the invention, an auto-injector serves for administering a dose of a liquid medicament. The auto-injector has a distal end and a proximal end with an orifice intended to be applied against an injection site. The auto-injector comprises:

an elongate housing arranged to contain a syringe with a hollow needle and a stopper for sealing the syringe and displacing the medicament, wherein the syringe is slidably arranged with respect to the housing, a drive means capable of, upon activation:

pushing the needle from a covered position into an advanced position through the orifice and past the proximal end, and operating the syringe to supply the dose of medicament, and activating means arranged to lock the drive means in a compressed state prior to manual operation and capable of, upon manual operation, releasing the drive means for injection.

In the context of this specification the term "proximal" refers to the direction pointing towards the patient during an injection while the term "distal" refers to the opposite direction pointing away from the patient. When referring to the proximal and distal portion of the auto-injector their respective distal and proximal ends are those that point in the respective direction during an injection.

In the auto-injector according to the invention a shroud is arranged at least partially inside the housing. The shroud is slidable in longitudinal direction between at least a retracted position, in which the needle is exposable and an advanced position, in which the needle is covered by the shroud. The shroud is arranged to be locked in the retracted position prior to manual operation of the activation means. Once the drive means has been released the shroud is unlocked and automatically moves towards the advanced position under load of a syringe spring. This automatic movement will happen when the auto-injector is removed from the injection site in the course of an injection or after the injection has been completed in order to hide the needle and keep the user from injuring themselves. As long as the user maintains the auto-injector pressed against the injection site during the injection cycle, the shroud will remain in the retracted position. A protective needle shield is attachable to the needle in a manner to partially protrude beyond the proximal end of the shroud through the orifice with the needle in its advanced position, which may be an "as shipped" state of the auto-injector. A syringe carrier is arranged inside the shroud for holding the syringe. The syringe carrier is slidable with respect to the shroud. The syringe carrier comprises at least one resilient snap for locking it to the shroud in order to prevent relative axial motion. The snap is arranged to be supportable from inside by the protective needle shield when attached to the needle in order to remain engaged with the shroud. The snap is inwardly biased to disengage from the shroud without support from inside in a manner to automatically disengage upon removal of the protective needle shield. Once the snap is disengaged, the syringe spring retracts the syringe carrier, the syringe and the needle into the covered position with the needle hidden inside the shroud. In the state as shipped the auto-injector is needle safe due to the protective needle shield hiding the needle. With the syringe and needle retracting immediately upon removal of the protective needle shield the auto-injector remains needle safe when armed.

The shroud may be slidable from the retracted position in the distal direction into an unlocking position by a small distance against the bias of at least one flexural element which may be arranged at the shroud. Furthermore, interlocking means may be arranged to allow the activating means to be operated only, when the shroud is in the unlocking position, wherein the interlocking means are arranged to prevent the activating means from being operated otherwise. Thus, a skin interlock feature is provided for making sure, the auto-injector is properly positioned against the injection site before allowing the injection to be triggered by the user.

At least one resilient latch may be arranged on the shroud for engaging in a respective recess of the housing when the shroud is translated into its advanced position. Thus, post-injection needle safety is improved since the shroud cannot be pushed in distal direction again after the end of an injection cycle. In both cases, when the auto-injector is removed from the injection site during injection or after delivering the full dose the needle is covered and is needle safe.

In a preferred embodiment a gearbox is arranged for converting a first translation into a second translation. The gearbox comprises a drive collar connectable to the translative drive means, the drive collar prevented from rotating with respect to a ground of the drive means, which may be a housing or chassis or a grounding member fixed thereto. A drive sleeve is rotatably arranged at least partially inside the drive collar, engaged to the drive collar by a first screw thread and prevented from translating relative to the ground. A plunger is arranged at least partially inside the drive sleeve, engaged to the drive sleeve by a second screw thread and prevented from rotating. The plunger is the component for outputting the second translation. The gearbox is arranged between the drive means and the syringe or the stopper in order to adapt the force of the compression spring to the requirements of an injection.

The gearbox can modify, i.e. both reduce and amplify the distance and force of the second translation relative to the first translation.

The drive means of the auto-injector is preferably arranged as a compression spring grounded at a distal end in a grounding member fixed to the housing, wherein a proximal end of the compression spring bears against the drive collar.

When applied in an auto-injector with a compression spring as the drive means, the gearbox can be used to modify an amount of spring force that is transmitted to a syringe or a stopper of the syringe.

Thus the spring force may be softened at the beginning of an injection cycle when the spring force is highest in order to reduce impact loads experienced by components within the auto-injector. When applied directly to a glass syringe, the risk of breaking the glass by impact is remarkably reduced. Furthermore, user discomfort related to high impact loads is reduced. The dispense characteristics of the auto-injector may be varied, e.g. in order to provide a rapid needle insertion, which is believed to offer benefits in terms of reducing the amount of pain felt by the patient. Furthermore, by adapting the transmitted force the dose may be delivered more steadily and the repeatability of the time required for the injection cycle is improved. Otherwise, if the cycle times are highly variable between different auto-injectors of the same type, the user may be confused and make errors when delivering the injection. The force available from the drive means may be modified for particular operations of the device, e.g. steps in the operational cycle, such as operating a latch mechanism to trigger needle retraction, may require a higher force, so the gearbox may be tailored to deliver the required force. Particularly with a compression spring used as the drive means the spring force decays with increasing extension of the spring. The gearbox may be adapted to compensate that decay. This may be used to eliminate the compromise between achieving a high end of dose load and minimizing the initial spring load. A dose delivery flow rate may be kept constant.

The first screw thread and the second screw thread are like-handed, i.e. both right-handed or both left-handed.

In an alternative embodiment the drive sleeve may have an internal screw thread engaged with the plunger and the drive collar may have an internal screw thread engaged with the drive sleeve.

The modification of the second translation (output) force and travel relative to the first translation (input) is preferably achieved by varying a pitch angle of the first screw thread and/or the second screw thread over the length of the respective screw thread.

The first screw thread and/or the second screw thread may comprise a cam track in one of the engaged components and a ball or a follower in the other one of the engaged components. A ball held in a pocket in the respective component is preferred for its lower friction compared to a follower or peg. The screw threads may likewise have multiple parallel cam tracks, i.e. multi-start threads in order to distribute load to the respective number of followers or balls so the individual point load for each follower or ball is reduced thereby improving the stability of the mechanism and the smoothness of the transmission.

In one embodiment of the invention a number of teeth are circumferentially arranged on an external surface of the drive sleeve. A section of the shroud has internal splines for engaging with the teeth in order to prevent rotation of the drive sleeve when the shroud is in its advanced position. Another section of the shroud proximally adjacent to the splined section is arranged to allow rotation of the drive sleeve. This feature allows for immediately stopping delivery of the medicament upon removal of the auto-injector from the injection site prior to full dose delivery. This avoids continued displacement of medicament from the syringe after removing the auto-injector from the injection site.

In an alternative embodiment of the invention, a transmission arrangement for controlling a force of the drive means is provided instead of the gearbox between the drive means and the syringe and/or the stopper.

The transmission arrangement comprises a drive collar connectable to a translative drive means and prevented from rotating with respect to a ground of the drive means which may be the housing or a chassis or a grounding member fixed thereto. A flange face of the drive collar bears against a mating flange face of a friction collar. The friction collar is slidable in longitudinal direction and rotationally constrained by engagement in a cam track. Another flange face of the friction collar bears against a mating flange face of a plunger. The plunger is slidable in longitudinal direction and prevented from rotating.

The plunger is the component for outputting the translation modified by the transmission arrangement.

Rotation of the friction collar is defined by a pitch angle of the cam track. The load on the friction collar is coupled to the rotationally fixed, axially free plunger. The force of the drive means acting on both mating surfaces of the friction collar towards the drive collar and towards the plunger introduces a friction force opposing rotation. As the friction collar axially translates, it is forced to rotate by any section of the cam track that is not parallel with a longitudinal axis. The friction collar will only rotate if the friction force between the mating surfaces of the drive collar and the plunger is overcome. The torque to overcome this friction force is generated by the contact force between the cam follower and the cam track, in which the cam follower is engaged. The contact force is generated by the spring force of the drive spring. A degree of coupling between the spring force and the contact force is defined by the respective pitch angle of the cam track. By an appropriate modification to the cam track angle, the amount of spring force required to overcome the friction force can be modified. For instance, increasing the cam angle requires more of the spring force to be reacted through the cam track, thereby reducing the force of the translation. The friction force is zero in straight sections of the cam track in parallel with a longitudinal axis of the overall arrangement. With any non-zero pitch angle the friction force is introduced.

When applied in an auto-injector with a compression spring as the drive means, the transmission arrangement can be used to modify an amount of spring force that is transmitted to a syringe or a stopper of the syringe.

Thus the spring force may be softened at the beginning of an injection cycle when the spring force is highest in order to reduce impact loads experienced by components within the auto-injector. When applied directly to a glass syringe, the risk of breaking the glass by impact is remarkably reduced. Furthermore, user discomfort related to high impact loads is reduced. The dispense characteristics of the auto-injector may be varied, e.g. in order to provide a rapid needle insertion, which is believed to offer benefits in terms of reducing the amount of pain felt by the patient. Furthermore, by adapting the transmitted force the dose may be delivered more steadily and the repeatability of the time required for the injection cycle is improved. Otherwise, if the cycle times are highly variable between different auto-injectors of the same type, the user may be confused and make errors when delivering the injection. The force available from the drive means may be modified for particular operations of the device, e.g. steps in the operational cycle, such as operating a latch mechanism to trigger needle retraction, may require a higher force, so the transmission arrangement may be tailored to deliver the required force. Particularly with a compression spring used as the drive means the spring force decays with increasing extension of the spring. The transmission arrangement may be adapted to compensate that decay by a pitch angle converging towards a straight, longitudinal section of the cam track, so at the end of the movement the full force of the compression spring is available. Thus a dose delivery flow rate may be kept constant.

The drive means may be a compression spring arranged over a shaft of a grounding member. The drive collar and the friction collar may be arranged in series with the compression spring and grounding member. The cam track may be arranged in an external surface of the shaft the pin and a cam follower for engaging in the cam track may be arranged on the friction collar.

Preferably the pitch angle of the cam track is varied over its length in order to achieve the desired force of the translation.

There may be more than one cam track on the ground member shaft, the different cam tracks with different pitch angle profiles, so the force control may be customized by selecting one of the cam tracks for engaging with the friction collar.

Instead of the planar flange faces the plunger, drive collar and friction collar may have profiled or curved flange faces. In this case, rotation of the friction collar would introduce additional force control by the varying angles of the mating faces. At the same time the distance travelled by the plunger may be amplified or reduced by modifying an overall length of the drive collar, friction collar and plunger when the friction collar is rotated.

The friction collar and the shaft of the grounding member may be arranged to provide a ratchet feature to generate an audible user feedback when the friction collar advances. Small raised features can be spaced in the cam track over which the follower has to pass. These features can be profiled such that they induce vibration into the device as the dose is delivered.

In a preferred embodiment the plunger may comprise at least a hollow portion arranged for fitting onto the ground member shaft. Thus, the shaft serves for centring all components. The hollow portion may have apertures in order to avoid the generation of a vacuum in the hollow portion when the plunger is being pushed off the shaft during the translation.

The hollow portion of the plunger may comprise an internal cam follower for engaging in one of the straight, longitudinal sections of the cam track, thus preventing rotation of the plunger.

In order to interlock the activation means or trigger button with the shroud at least one snap arm may be distally arranged at the drive collar in a manner to be engageable behind a shoulder on the grounding member in order to prevent expansion of the drive means. The snap arm may be disengageable from the shoulder by being pushed outward by a respective resilient extension of a trigger button. The resilient extension may be arranged to be flexed outward by pushing the trigger button in proximal direction thereby moving the resilient extension along a tapering surface of the grounding member which forces the resilient extension outwards. The shroud may be arranged to prevent at least one of the resilient extensions from flexing outwards when the shroud is its retracted position. At least one distal recess may be arranged in the shroud for allowing a respective resilient extension to be flexed outwards through the recess or aperture when the shroud is in an unlocking position.

The syringe spring may be arranged to bear against an internal shoulder in the shroud between a distal portion and a proximal portion and against a rear flange of the syringe carrier.

An intermediary component may be arranged for forwarding translation of the plunger to the syringe in order to first advance the syringe and needle while avoiding load onto the stopper thus avoiding wet injection, i.e. medicament leaking out of the needle's tip before the needle is fully inserted into the injection site. The intermediary component is furthermore arranged to be decoupled from the syringe when the needle has reached a predefined injection depth. At the same time the translation is coupled to the stopper in order to inject the dose.

The term "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, a antibody, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38[Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp(O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein:

FIG. 7 is the auto-injector during removal from the injection site in the course of an injection.

Corresponding parts are marked with the same reference symbols in all figures.

DETAILED DESCRIPTION

Figure 1A:
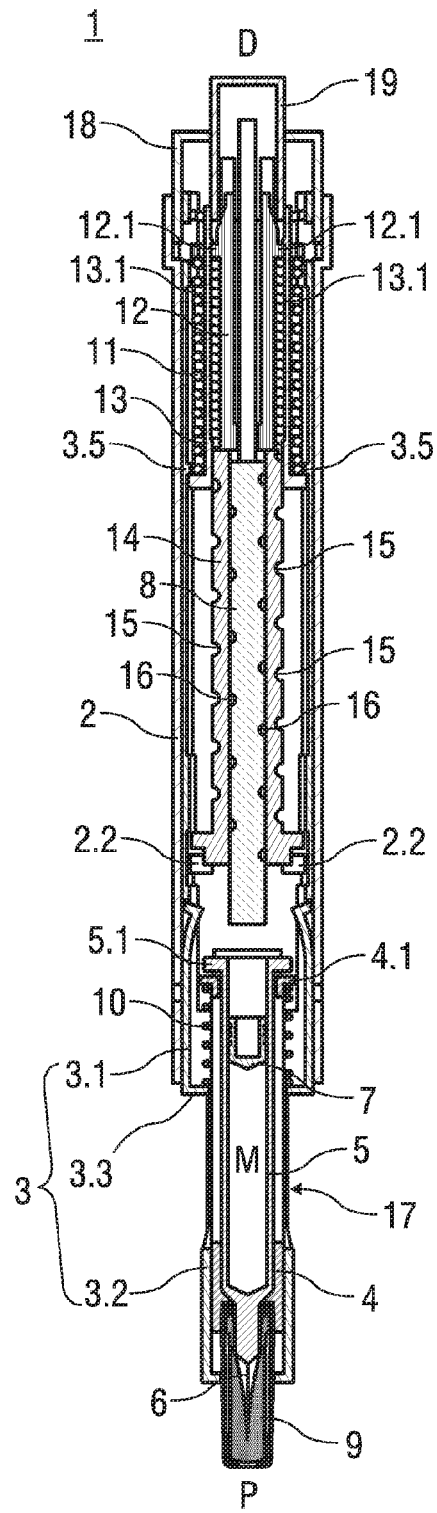
FIG. 1 is longitudinal sections in two section planes of an auto-injector with force control in an as shipped state.
Figure 1B:
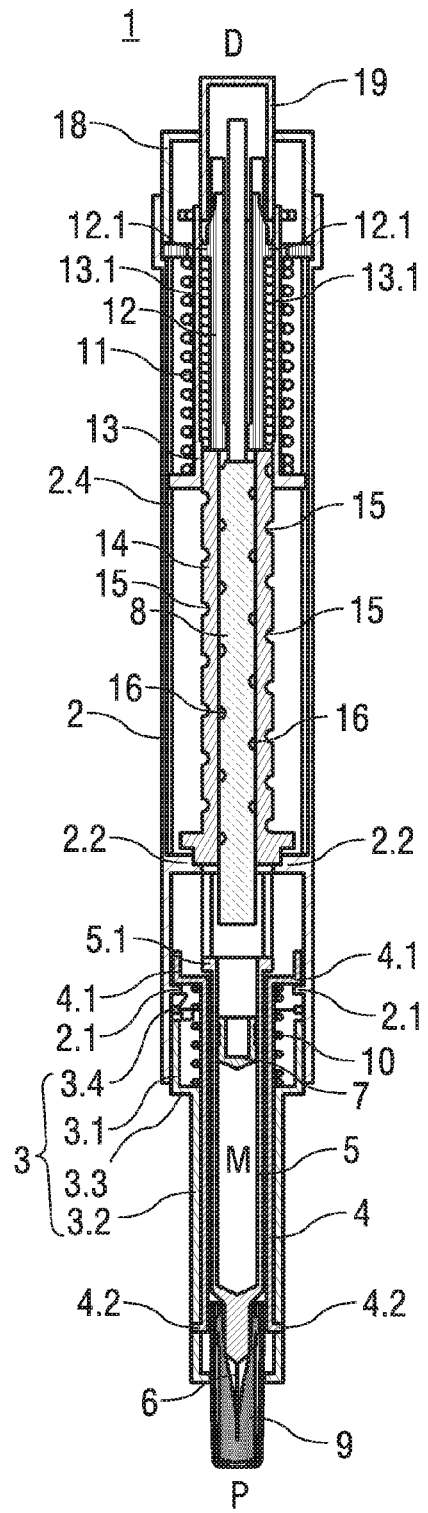

FIG. 1 shows two longitudinal sections in two section planes of an auto-injector 1 with force control in an as shipped state. The auto-injector 1 comprises an elongate housing 2, an essentially tubular shroud 3 arranged inside the housing 2 and slidable in longitudinal direction with respect to the housing 2. A distal portion 3.1 of the shroud has an external diameter selected to fit into the housing 2. The distal portion 3.1 extends essentially through the entire housing 2 to the distal end D. The biggest part of the distal portion 3.1 consists of two longitudinal extensions rather than a tube shape in order to allow other parts of the auto-injector 1 to engage in the housing 2 for preventing relative rotation. This could alternatively be achieved by a tubular distal portion 3.1 with longitudinal slots. A proximal portion 3.2 of the shroud 3 has a reduced diameter compared to the distal portion 3.1 for slidably accommodating a syringe carrier 4. The syringe carrier 4 holds a syringe 5 and supports it at its proximal end in order to avoid stress to its finger flanges 5.1. A hollow injection needle 6 is attached to the proximal end of the syringe 5. A stopper 7 serves for sealing the distal end of the syringe 5. A liquid medicament M stored in the syringe 5 may be displaced through the needle 6 by pushing the stopper 7 in proximal direction P by means of a plunger 8. In the as shipped state the syringe 5 and syringe carrier 4 are locked in position thus providing a clearance between the plunger 8 and the stopper 7. Although the needle 6 protrudes beyond the proximal end P of the auto-injector 1, needle stick injuries are avoided by a protective needle shield 9 attached to the needle 6 in the as shipped state. The syringe carrier 4 is biased in distal direction D with respect to the shroud 3 by means of a syringe spring 10 bearing against a shoulder 3.3 in the shroud 3 and against a rear flange 4.1 in the syringe carrier 4. The shoulder 3.3 is defined between the distal portion 3.1 and the proximal portion 3.2. The rear flange 4.1 is arranged at the distal end of the syringe carrier 4. A drive spring 11 is arranged near the distal end D of the auto-injector 1 inside the shroud 3. The drive spring 11 is preferably arranged as a compression spring. The distal end of the drive spring 11 is grounded in the housing 2 or in a grounding member 12 fixed to the housing 2. The proximal end of the drive spring 11 bears against a drive collar 13 which is arranged inside the drive spring 11, rotationally fixed by splines 2.4 in the housing 2 but translatable in longitudinal direction. Inside the drive collar 13 a drive sleeve 14 is arranged which in turn is arranged around the plunger 8. The drive sleeve 14 is rotationally free and axially fixed by distally bearing against the grounding member 12 and proximally bearing against a second bulkhead 2.2. The plunger 8 is rotationally fixed and axially free. The drive collar 13 is engaged with the drive sleeve 14 by a first screw thread 15. The drive sleeve 14 is engaged with the plunger 8 by a second screw thread 16. Hence, when the drive collar 13 is pushed in proximal direction P by the drive spring 11, the drive sleeve 14 is caused to rotate which causes axial movement of the plunger 8. The first screw thread 15 and the second screw thread 16 are like-handed. By varying the pitch of the two screw threads 15, 16 a ratio of translation of the drive collar 13 and the plunger 8 is changed and hence the transmitted force is amplified or reduced.

The screw threads 15, 16 may have cam tracks and followers or ball bearings.

A syringe viewing window 17 for inspecting the syringe contents is provided in the proximal portion 3.2 of the shroud 3.

A housing cap 18 and a trigger button 19 are arranged at the distal end D of the auto-injector 1.

Figure 1C:
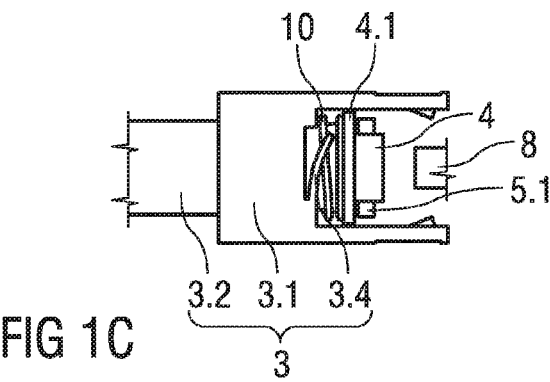

In the shipped state in FIG. 1, the drive spring's 11 preload on the drive collar 13 is statically resolved through distal snap arms 13.1 of the drive collar 13 which are engaged behind a shoulder 12.1 in the grounding member 12. The syringe carrier 4 is prevented from moving in proximal direction P by the rear flange 4.1 bearing against a first bulkhead 2.1 provided in the housing 2. Withdrawal of the shroud 3 into the housing 2 is resisted by flexural elements 3.4 on the shroud 3 acting against the first bulkhead 2.1 of the housing 2 from the proximal side (see FIG. 1c for details). Extension of the shroud 3 in proximal direction P is prevented by inward protrusions 3.5 contacting the drive collar 13. The syringe carrier 4 is locked to the shroud 3 by at least two snaps 4.2.

The protective needle shield 9 is interlocked to the syringe carrier 4. For this purpose the syringe carrier 4 has a pair of resilient snaps 4.2 extending proximally beyond the section of the syringe carrier 4 supporting the proximal end of the syringe 5. In the state as shipped these snaps 4.2 are snapped into corresponding recesses provided in the proximal portion 3.2 of the shroud 3 thus preventing relative axial translation between the shroud 3 and the syringe carrier 4. The snaps 4.2 are kept from flexing inwards and disengaging from the recesses by the protective needle shield 9. The protective needle shield 9 protrudes beyond the proximal end of the shroud 3 through an orifice.

Figures 2, 3:
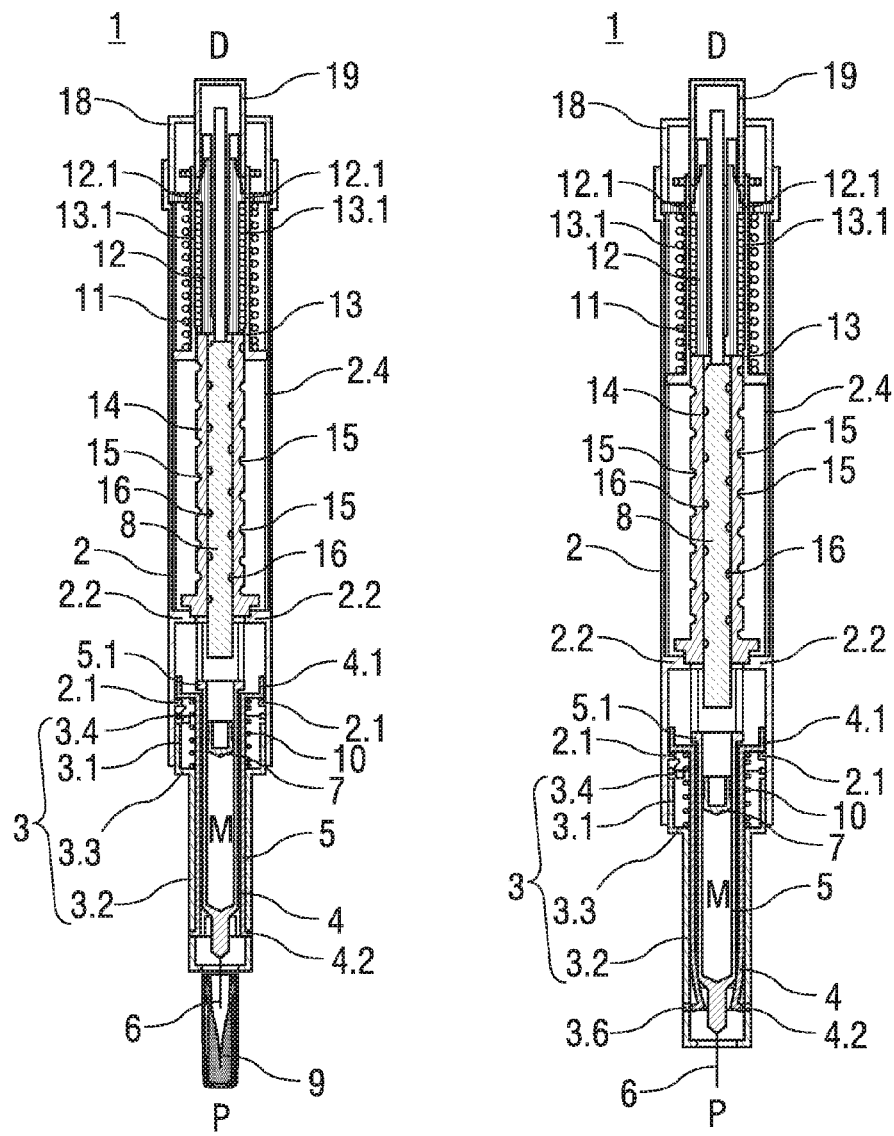
FIG. 2 is the auto-injector during removal of a protective needle shield.
FIG. 3 is the auto-injector with a syringe carrier delatching from a shroud following the removal of the protective needle shield.

In order to arm the auto-injector 1 the protruding part of the protective needle shield 9 is gripped by a user and pulled off the syringe 5 and needle 6 in proximal direction P (see FIG. 2). Once the protective needle shield 9 has been removed the snaps 4.2 are no longer supported inwardly and disengage from the recesses 3.6 (see FIG. 3). Preferably the snaps 4.2 are biased to relax inwards when not supported. In an alternative embodiment the snaps 4.2 and the shroud 3 may have angled mating surfaces for moving the snaps 4.2 inward thus disengaging them from the recesses 3.6 under the force from the syringe spring 10 when the snaps 4.2 are not supported inwardly. In this case the snaps 4.2 do not have to be biased inwardly.

Figure 4A:
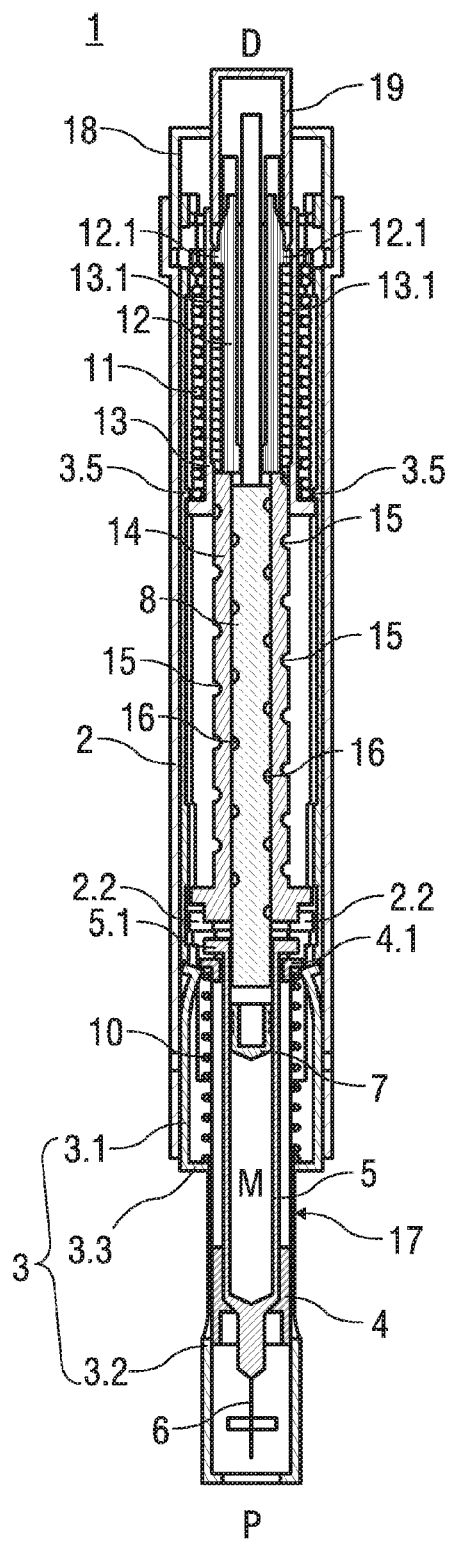
FIG. 4 is the auto-injector with the syringe carrier, syringe and a needle being retracted into the shroud after delatching.
Figure 4B:
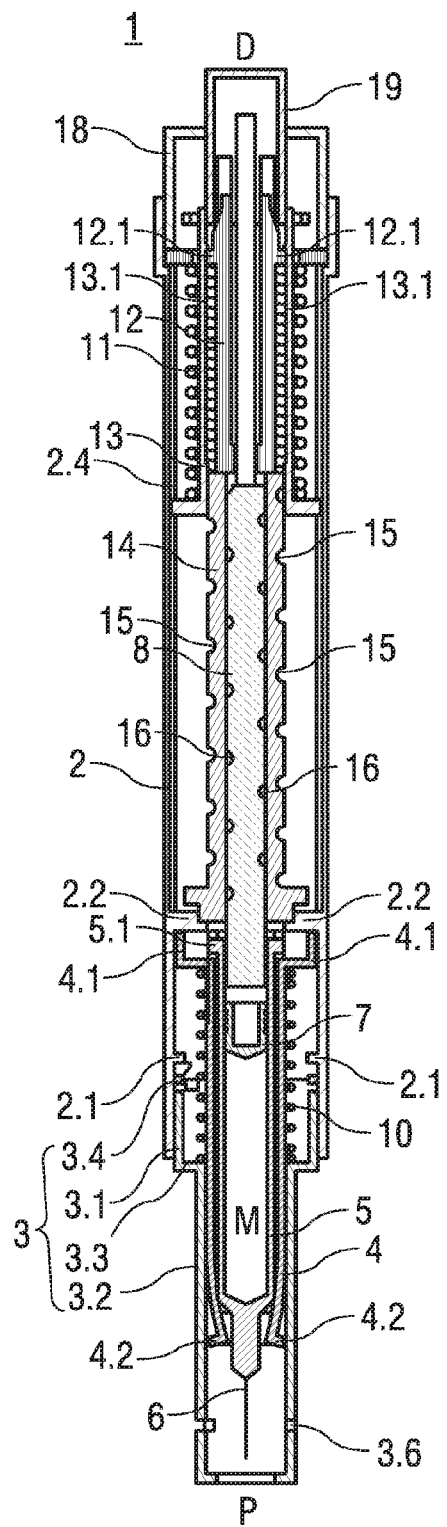

Now delatched from the shroud 3 the syringe carrier 4 together with the syringe 5 and the needle 6 are translated in distal direction D due to the load of the syringe spring 10 (see FIG. 4). Thus the needle 6 is hidden inside the shroud 3 and the user protected from accidental needle stick injuries.

Figure 5A:
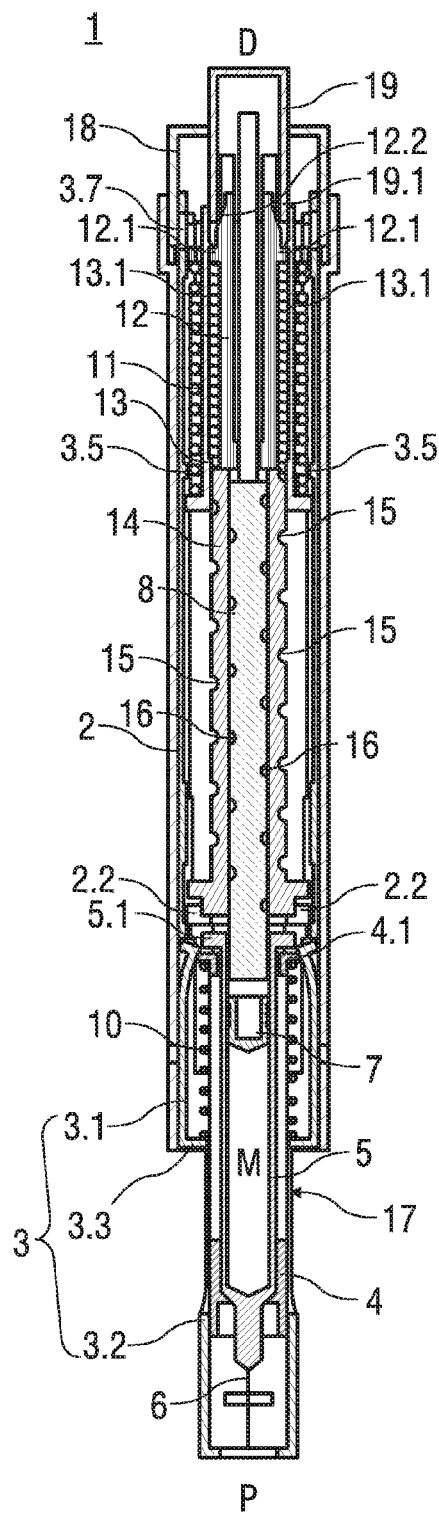
FIG. 5 is the auto-injector during deactivation of an interlock by pressing the shroud against an injection site.
Figure 5B:
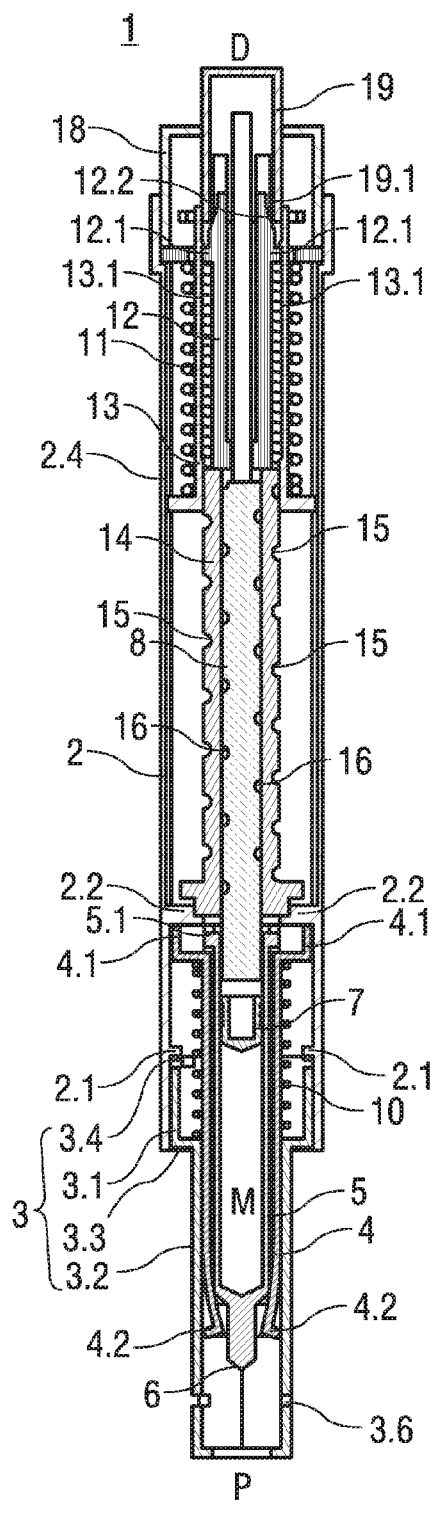
Figure 5C:
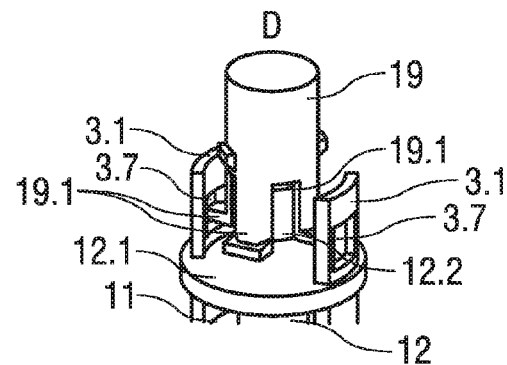

In the next operating step the user places the proximal end P of the auto-injector 1 against an injection site, e.g. a patient's skin. When contacting the injection site the shroud 3 is depressed and translates by a small distance in distal direction D into the housing 2 (see FIG. 5) against the load of the flexural elements 3.4. As the shroud 3 translates apertures in the shroud 3 move from a blocking position against trigger button resilient extensions 19.1, thus unlocking the trigger button 19.

The trigger button 19 comprises a number of resilient extensions 19.1 facing the grounding member 12. The grounding member 12 has a tapering surface 12.2 facing the trigger button 19. The resilient extensions 19.1 are at least partially arranged inside the snap arms 13.1 of the drive collar 13. When the trigger button 19 is pushed in proximal direction P the resilient extensions 19.1 contact the tapering surface 12.2 and are splayed apart. Consequently, the resilient snap arms 13.1 are also splayed apart and disengaged from the shoulder 12.1 of the grounding member 12. Thus, the drive collar 13 is no longer axially restricted and will be released in the proximal direction P by the drive spring 11.

Before the shroud 3 is depressed (FIGS. 1 to 4) the distal portion 3.1 of the shroud 3 prevents the trigger button's 19 resilient extensions 19.1 from splaying out. As the shroud 3 is depressed (FIG. 5) it travels in distal direction D to such an extend that the resilient extensions 19.1 meet respective distal recesses 3.7 thus allowing the resilient extensions 19.1 to be splayed apart (see FIG. 5c for details). At the same time the syringe spring 10 is partially compressed by depressing the shroud 3.

Figure 6A:
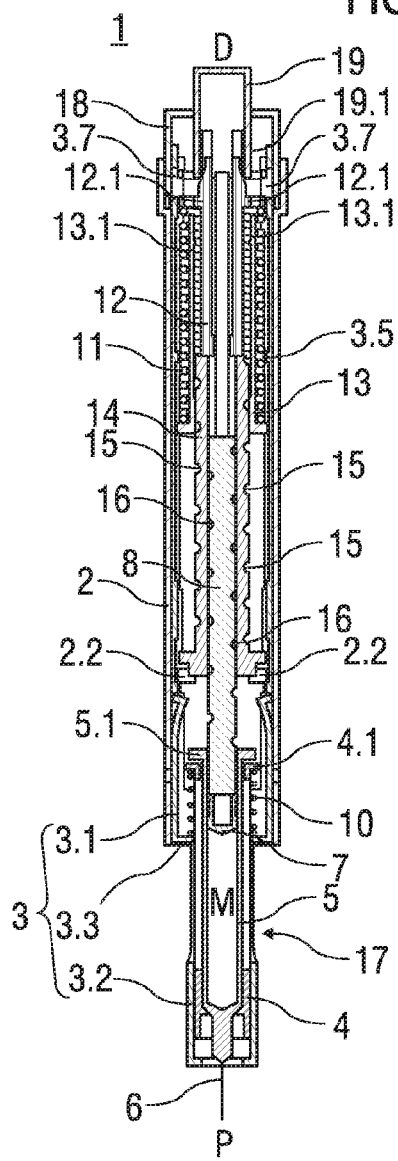
FIG. 6 is the auto-injector during needle insertion into the injection site.
Figure 6B:
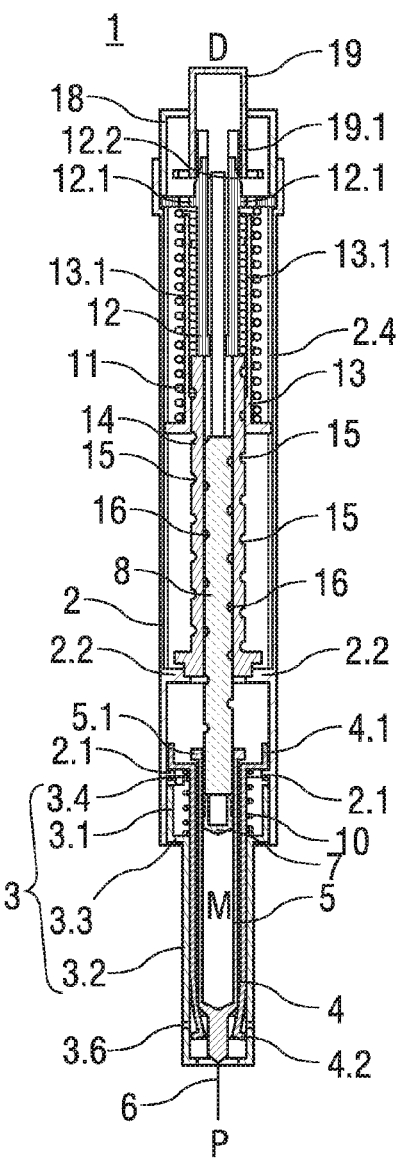

When the trigger button 19 is pressed and the drive collar 13 is delatched from the grounding member 12 the force of the drive spring 11 translates the drive collar 13 in proximal direction P (see FIG. 6). Rotation of the drive collar 13 is prevented by splined engagement in the housing 2. The drive sleeve 14 is forced to rotate by engagement to the drive collar 13 through the first screw thread 15. The plunger 8 extends towards the stopper 7 by engagement to the drive sleeve 14 through the second screw thread 16. The first screw thread 15 may comprise an external, right-handed screw thread in the drive sleeve 14 engaged with a ball located in a pocket on the internal surface of the drive collar 13. The second screw thread 16 may comprise an external right-handed screw thread in the plunger 8 engaged with a ball located in a pocket on the internal surface of the drive sleeve 14. Alternatively, both screw threads 15, 16 may be left-handed. Rotation of the plunger 8 is prevented by splined engagement in the grounding member 12. This may be achieved by corresponding non-circular cross sections, e.g. square cross sections.

The gear ratio of the gear box comprising the drive collar 13, the first screw thread 15, the drive sleeve 14 and the second screw thread 16 is defined by the pitch angles of the two screw threads 15, 16. If the pitch angle of the drive sleeve 14 is greater than that of the plunger 8, the gear ration will be greater than 1, i.e. the gear box acts as a distance multiplier. Conversely, when the plunger 8 pitch angle is greater than that of the drive sleeve 14, the gear ratio will be less than 1, i.e. the gear box acts as a force multiplier.

In an alternative embodiment the drive sleeve 14 may have an internal screw thread engaged with the plunger 8 and the drive collar 13 may have an internal screw thread engaged with the drive sleeve 14.

As the plunger 8 travels forward it meets the stopper 7 and applies a force on it which is resolved through the syringe spring 10. The counteracting force of the syringe spring 10 during compression has to be greater than a counteracting force of the stopper 7 due to friction between the stopper 7 and the inner wall of the syringe 5 and due to the hydrostatic resistance of the liquid medicament M to be displaced through the hollow needle 6. As the syringe spring 10 is compressed the syringe carrier 4 travels in proximal direction P together with the syringe 5 and the needle 6. Hence, the needle 6 is inserted into the injection site. The injection depth is set by the rear flange 4.1 of the syringe carrier 4 contacting the first bulkhead 2.1.

When the rear flange 4.1 hits the first bulkhead 2.1 the force of the plunger 8 pushes the stopper 7 in proximal direction P thus displacing the liquid medicament M from the syringe 5 through the needle 6 and into the injection site. During injection of the medicament M, the pitch angles of the screw threads 15, 16 may vary in order to adapt the mechanical advantage of the gearbox.

FIGS. 7a and 7c show the auto-injector 1 during removal from the injection site in the course of an injection cycle. If this happens, the shroud 3 will extend to cover the needle 6 under load of the syringe spring 10. In parallel, internal splines 3.8 on the distal part 3.1 of the shroud 3 engage in teeth 14.1 on the outer surface of the drive sleeve 14. This prevents further rotation of the drive sleeve 14 and hence expansion of the plunger 8 and further emptying of the syringe 5. FIG. 7b shows the drive sleeve 14 and the shroud 3 during injection with the shroud 3 persistently pressed against the injection site. Hence, the splines 3.8 and teeth 14.1 do not engage and the drive sleeve 14 continues rotating. By contrast, FIG. 7c shows the drive sleeve 14 and the shroud 3 during removal of the auto-injector 1 from the injection site in the course of an injection cycle. The shroud 3 is translated in proximal direction P to an extent bringing the teeth 14.1 and the splines 3.8 into engagement.

Even though the forward extension of the shroud 3 is limited by the position of the drive collar 13, the auto-injector 1 is configured to provide needle safety at all stages of the operational cycle:

With a transmission ratio of 1 or less as illustrated, as the needle is inserted into the injection site, the drive collar 13 moves in sync with the syringe 5. Therefore, given that the needle 6 is initially fully covered when the shroud 3 is fully extended and the needle 6 moves in sync with the drive collar 13, the needle can not protrude a greater distance from the shroud 3 than the distance permitted by the drive collar 13 and the inward protrusions 3.5. If the transmission ratio were greater than 1, the design may be modified to position the needle 6 further from the proximal end of the shroud 3 to ensure needle safety at all stages of the injection.

Figure 8A:
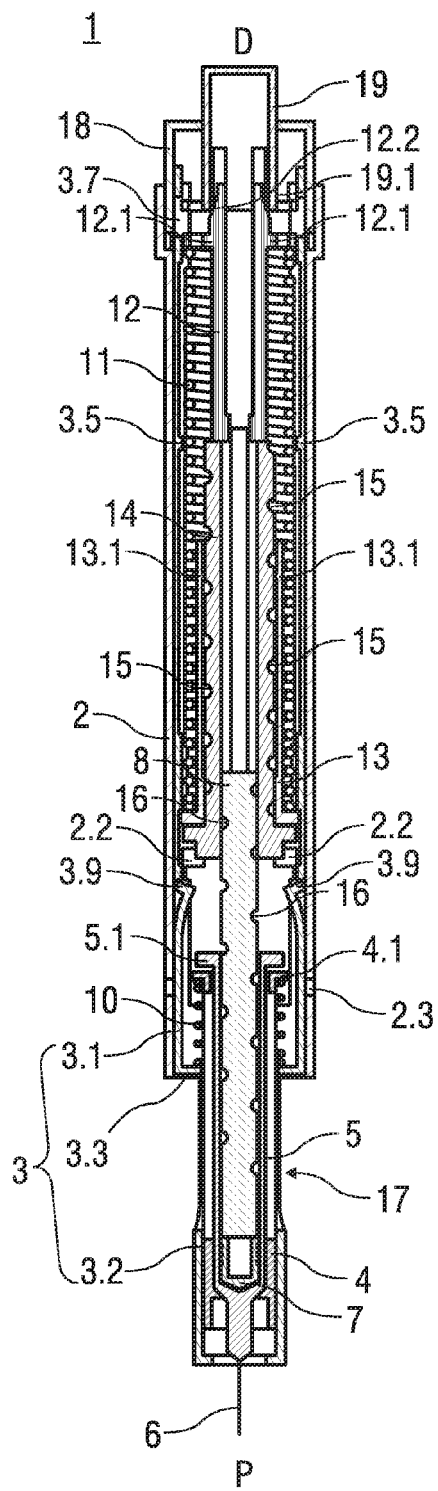
FIG. 8 is the auto-injector near the end of the injection.
Figure 8B:
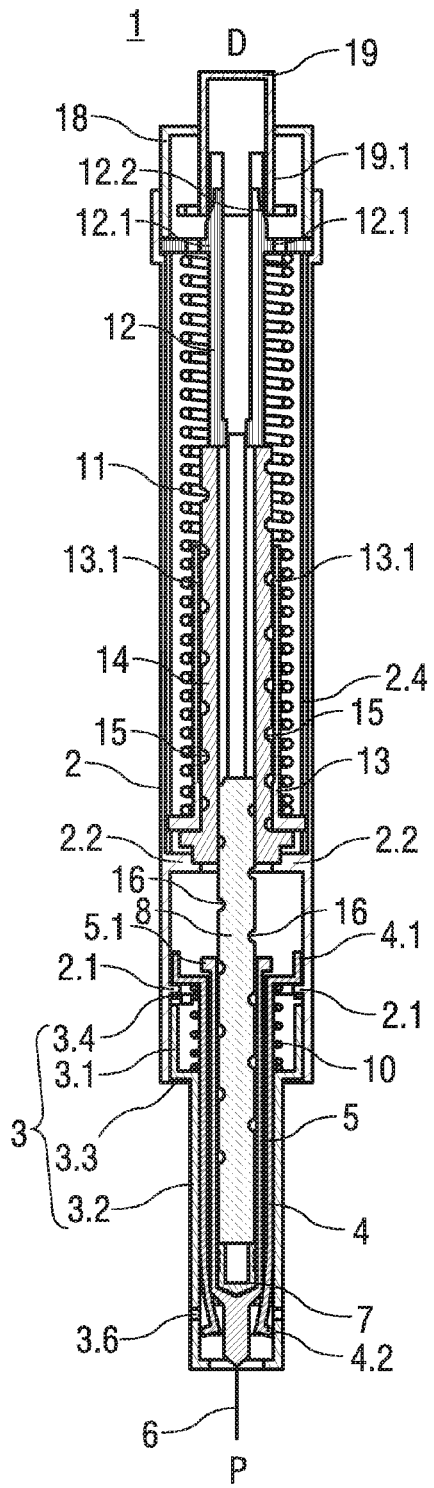

In FIG. 8 the stopper 7 has reached the end of the syringe 5 and the dose is fully delivered. The auto-injector 1 is sized so that this occurs prior to the drive collar 13 and/or plunger 8 reaching end-of-travel on their respective screw threads 15, 16, in particular before a flange 13.2 of the drive collar 13 contacts a flange 14.2 of the drive sleeve 14. The end of dose may be indicated to the user by an elapsed time (e.g. ten seconds), visible inspection through the syringe viewing window 17, or audible detection of movement of a ratchet engaged between any two parts with relative motion, for example the housing 2 and the drive sleeve 14.

Figure 9:
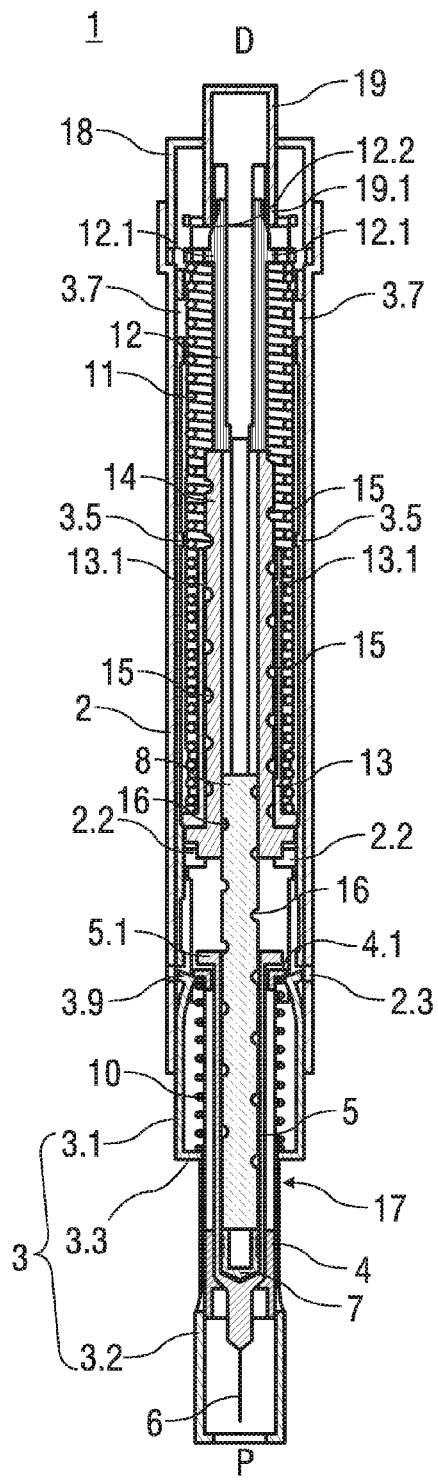
FIG. 9 is the auto-injector withdrawn from the injection site after having completed the injection, wherein the shroud extends to cover the needle.

When the dose has been fully delivered the user may remove the auto-injector 1 from the injection site thus extracting the needle 6. As the auto-injector 1 is removed, the shroud 3 extends under bias of the syringe spring 10 (see FIG. 9).

Figure 10:
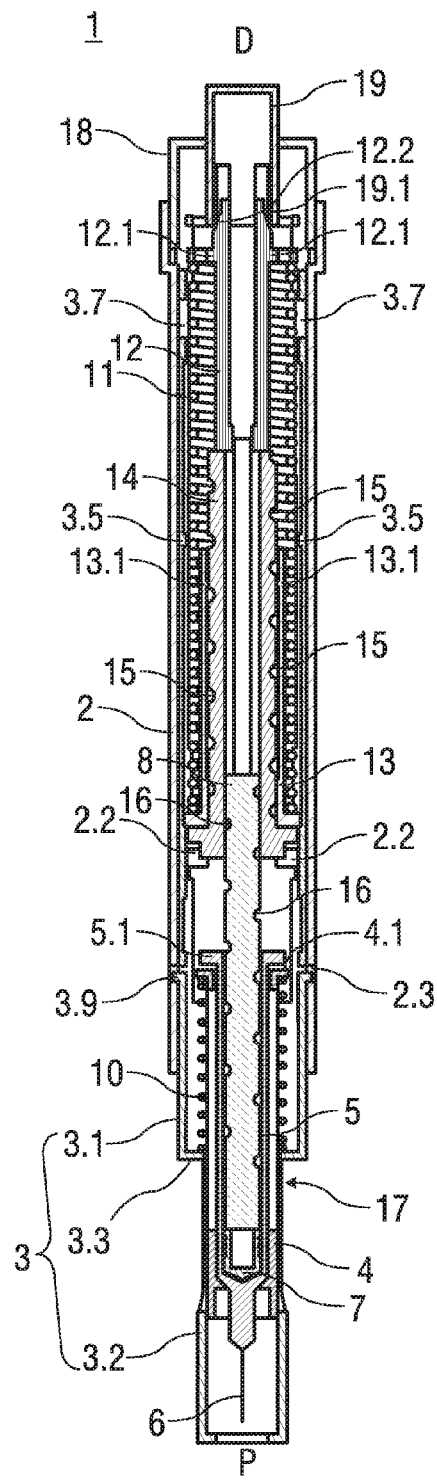
FIG. 10 is the auto-injector with the shroud locking into the housing.

When the shroud 3 is at least almost fully extended, resilient latches 3.9 in the distal portion 3.1 of the shroud 3 snap into respective recesses 2.3 arranged in the housing 2 thus preventing the shroud 3 from being pushed in distal direction D again, so post injection needle safety is provided (FIG. 10). This applies for both cases, when the auto-injector 1 is removed from the injection site during injection (FIG. 7a) or after delivering the full dose (FIG. 8).

The syringe carrier 4 has lateral apertures corresponding to the syringe viewing window 17 in order to allow visual inspection of the syringe 5.

Figure 11:
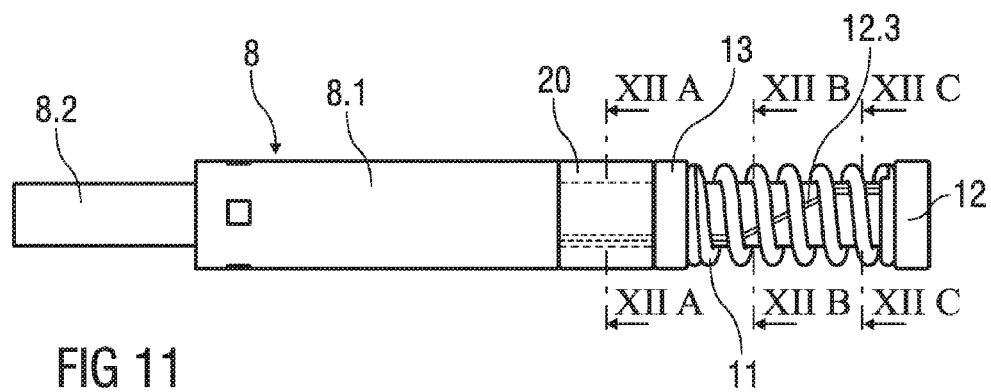
FIG. 11 is a lateral view of a detail of an alternative embodiment of an auto-injector with force control with a friction collar, FIG. 12 are three cross sections of the detail of FIG. 11.
Figures 12A, 12B, 12C:
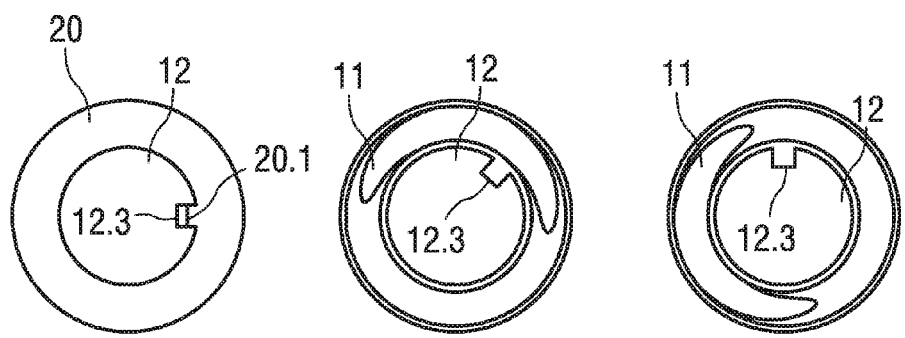
Figure 13:
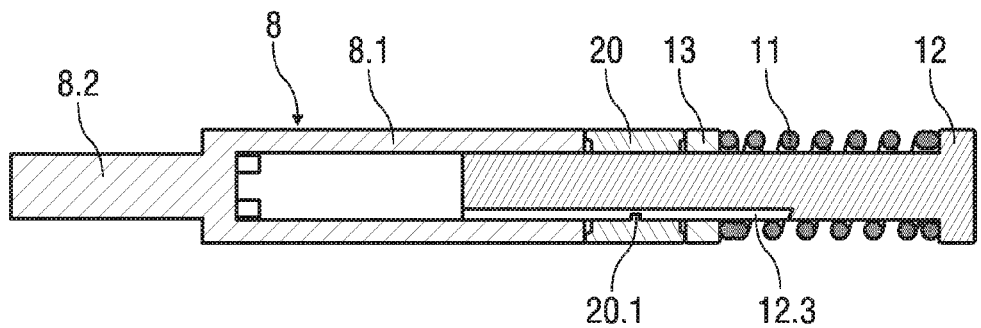
FIG. 13 is a longitudinal section of the detail of FIG. 11.

In another embodiment the gearbox as shown in the preceding figures comprising the drive collar 13, the first screw thread 15, the drive sleeve 14 and the second screw thread 16 may be replaced by a rotary friction element shown in FIGS. 11 to 13. The rotary friction element comprises a friction collar 20. In this embodiment the drive spring 11 bears against the drive collar 13 which in turn pushes against the friction collar 20 in sync with the plunger 8. At predetermined times the friction collar 20 is forced to rotate by its engagement in a cam track 12.3 provided in the grounding member 12. For this purpose the friction collar 20 has a cam follower 20.1.

As in the gearbox (FIG. 1) the drive collar 13 is rotationally fixed and axially free. The friction collar 20 in contrast is axially free and rotationally constrained by friction and by the cam track 12.3. The plunger 8 comprises a hollow distal portion 8.1 fitting onto a shaft of the grounding member 12 and a proximal portion 8.2 with a reduced diameter. The cross sections of both the hollow distal portion 8.1 and the shaft of the grounding member 12 may be designed to prevent rotation of the plunger 8. For instance the plunger 8 may have a cam follower running in a straight section of the cam track 12.3. Rotation of the friction collar 20 is defined by the cam track 12.3. The load on the friction collar 20 is coupled to the rotationally fixed, axially free plunger 8 which applies a force to the stopper 7. The compressive force of the drive spring 11 acting on both mating surfaces of the friction collar 20 towards the drive collar 13 and towards the plunger 8 introduces a friction force opposing rotation. As the friction collar 20 axially translates, it is forced to rotate by any section of the cam track 12.3 that is not parallel with the longitudinal axis of the auto-injector 1. The friction collar 20 will only rotate if the friction force between the mating surfaces of the drive collar 13 and the plunger 8 is overcome. The torque to overcome this friction force is generated by the contact force between the cam follower 20.1 and the cam track 12.3, in which the cam follower 20.1 is engaged. The contact force is generated by the spring force of the drive spring 11. A degree of coupling between the spring force and the contact force is defined by the respective angle of the cam track 12.3. By an appropriate modification to the cam track angle, the amount of spring force required to overcome the friction force can be modified. For instance, increasing the cam angle requires more of the spring force to be reacted through the cam track 12.3, thereby reducing the force applied to the stopper 7.

In an alternative embodiment an intermediary component may be provided for first coupling the plunger 8 to the syringe carrier 4 or the syringe 5 directly without acting on the stopper 7 until the needle 6 has reached its injection depth. The plunger 8 would then be decoupled from the syringe 5 or syringe carrier 4 by the intermediary component and instead be coupled to the stopper 7 in order to displace the medicament M from the syringe 5. Thus, wet injection is avoided, i.e. the medicament is not leaking out of the needle tip before the needle is inserted. The intermediary component may be a transfer sleeve or an additional feature at the syringe carrier 4. The transfer sleeve and plunger 8 would be initially coupled and translate together. However, when the syringe carrier 4 nears the end of its travel during needle insertion, the transfer sleeve would decouple from the plunger. From this point forwards, the plunger 8 load would be transferred directly to the stopper 7. This decoupling arrangement may be embodied in any suitable auto-injector arrangement. For example, the transfer sleeve could be clipped to the plunger by some clips. Near the end of travel the clips could find some place to splay or be pushed away from the plunger 8 in order to decouple the plunger 8 from the transfer sleeve.

The invention claimed is:

1. An auto-injector for administering a dose of a liquid medicament (M), the auto-injector having a distal end (D) and a proximal end P with an orifice intended to be applied against an injection site and comprising:
    an elongate housing arranged to contain a syringe with a hollow needle and a stopper for sealing the syringe and displacing the medicament (M), wherein the syringe is slidably arranged with respect to the housing,
    a driver capable of, upon activation:
        pushing the needle from a covered position into an advanced position through the orifice and past the proximal end (P), and
        operating the syringe to supply the dose of medicament (M), and
    a trigger mechanism arranged to lock the driver in a compressed state prior to manual operation and capable of, upon manual operation, releasing the driver for injection,
    characterized in that a shroud is arranged at least partially inside the housing, the shroud slidable in longitudinal direction between at least a retracted position, in which the needle is exposable and an advanced position, in which the needle is covered by the shroud, wherein the shroud is arranged to be locked in the retracted position prior to manual operation of the trigger mechanism and wherein the shroud is arranged to be pushed towards the advanced position by a syringe spring when the driver has been released, wherein a protective needle shield is attachable to the needle in a manner to partially protrude beyond the proximal end of the shroud through the orifice with the needle in its advanced position, wherein a syringe carrier is arranged inside the shroud for holding the syringe, the syringe carrier slidable with respect to the shroud, wherein the syringe carrier comprises at least one resilient snap for locking it to the shroud in order to prevent relative axial motion, wherein the snap is arranged to be supportable from inside by the protective needle shield when attached to the needle in order to remain engaged with the shroud and wherein the snap is inwardly biased to disengage from the shroud without support from inside in a manner to automatically disengage upon removal of the protective needle shield, thus allowing the syringe and needle to be retracted into the covered position under load of the syringe spring.

2. The auto-injector according to claim 1, characterized in that the shroud is slidable from the retractable position in distal direction (D) into an unlocking position by a small distance against the bias of at least one flexural element, wherein a plurality of protrusions are arranged to allow the trigger mechanism to be operated only, when the shroud is in the unlocking position, wherein the plurality of protrusions are arranged to prevent the trigger mechanism from being operated otherwise.

3. The auto-injector according to claim 1, characterized in that at least one resilient latch arranged at the shroud for engaging in a respective recess of the housing when the shroud is translated into its advanced position.

4. The auto-injector according to claim 1, characterized in that a gearbox for converting a first translation of the driver into a second translation of a plunger is arranged between the driver and the syringe or the stopper, the gearbox comprising a drive collar connectable to the driver and prevented from rotating with respect to a ground of the driver, a drive sleeve rotatably arranged at least partially inside the drive collar, engaged to the drive collar by a first screw thread and prevented from translating, wherein the plunger is arranged at least partially inside the drive sleeve, engaged to the drive sleeve by a second screw thread and prevented from rotating.

5. The auto-injector according claim 4, characterized in that a pitch angle of the first screw thread and/or the second screw thread vary/varies over the length of the respective screw thread.

6. The auto-injector according to claim 4, characterized in that the first screw thread and/or the second screw thread comprise a cam track in one of the engaged components and a ball or a follower in the other one of the engaged components.

7. The auto-injector according to claim 1, characterized in that teeth are circumferentially arranged on an external surface of the drive sleeve, wherein a section of the shroud has internal splines for engaging with the teeth in order to prevent rotation of the drive sleeve when the shroud is in its advanced position, wherein another section of the shroud proximally adjacent to the splined section is arranged to allow rotation of the drive sleeve.

8. The auto-injector according to claim 1, characterized in that a transmission arrangement for controlling a force of the translation of the driver is arranged between the driver and the syringe or the stopper, the transmission arrangement comprising a drive collar connectable to the translative driver and prevented from rotating with respect to a ground of the driver, a flange face of the drive collar bearing against a mating flange face of a friction collar, the friction collar slidable in longitudinal direction and rotationally constrained by engagement in a cam track, another flange face of the friction collar bearing against a mating flange face of a plunger, the plunger slidable in longitudinal direction and prevented from rotating.

9. The auto-injector according to claim 8, characterized in that the driver is a compression spring arranged on a pin of a grounding member, wherein the drive collar and the friction collar are arranged in series with the compression spring on the pin, wherein the cam track is arranged in the pin and wherein a cam follower for engaging in the cam track is arranged at the friction collar.

10. The auto-injector according to claim 8, characterized in that a pitch angle of the cam track is varied over its length.

11. The auto-injector according to claim 8, characterized in that the cam track comprises at least one straight, longitudinal section.

12. The auto-injector arrangement according to claim 8, characterized in that the plunger comprises at least a hollow portion arranged for fitting onto the pin.

13. The auto-injector according to claim 12, characterized in that the plunger comprises a cam follower for engaging in one of the straight, longitudinal sections of the cam track.

14. The auto-injector according to claim 4, characterized in that at least one snap arm is distally arranged at the drive collar in a manner to be engageable behind a shoulder on the grounding member in order to prevent expansion of the driver, the snap arm disengageable from the shoulder by being pushed outward by a respective resilient extension of a trigger button, the resilient extension arranged to be flexed outward by pushing the trigger button in proximal direction (P), thereby moving the resilient extension along a tapering surface of the grounding member, wherein the shroud is arranged to prevent at least one of the resilient extensions from flexing outwards when in the retracted position and wherein at least one distal recess is arranged in the shroud for allowing a respective resilient extension to be flexed outwards when the shroud is in its unlocking position.

\* \* \* \* \*